(12) United States Patent
Okuno et al.

(10) Patent No.: US 11,125,692 B2
(45) Date of Patent: Sep. 21, 2021

(54) DETERMINATION METHOD, DETERMINATION APPARATUS, AND RECORDING MEDIUM

(71) Applicant: HORIBA, LTD., Kyoto (JP)

(72) Inventors: Yoshito Okuno, Kyoto (JP); Daisuke Irikura, Kyoto (JP); Sakiko Akaji, Kyoto (JP); Shiro Miyake, Kyoto (JP)

(73) Assignee: HORIBA, LTD., Kyoto (JP)

( * ) Notice: Subject to any disclaimer, the term of this patent is extended or adjusted under 35 U.S.C. 154(b) by 0 days.

(21) Appl. No.: 16/771,987

(22) PCT Filed: Dec. 12, 2018

(86) PCT No.: PCT/JP2018/045591
§ 371 (c)(1),
(2) Date: Jun. 11, 2020

(87) PCT Pub. No.: WO2019/117177
PCT Pub. Date: Jun. 20, 2019

(65) Prior Publication Data
US 2021/0140891 A1    May 13, 2021

(30) Foreign Application Priority Data
Dec. 13, 2017   (JP) .............................. JP2017-238644

(51) Int. Cl.
*G01J 3/44* (2006.01)
*G01N 21/65* (2006.01)
*G06N 20/10* (2019.01)

(52) U.S. Cl.
CPC ............ *G01N 21/65* (2013.01); *G01J 3/4412* (2013.01); *G06N 20/10* (2019.01)

(58) Field of Classification Search
CPC ................. G01N 21/65; G01N 21/658; G01N 2021/656; G01J 3/02; G01J 3/44
(Continued)

(56) References Cited

U.S. PATENT DOCUMENTS

2011/0317158 A1   12/2011   Lyng et al.
2018/0327699 A1   11/2018   Ota et al.

FOREIGN PATENT DOCUMENTS

JP    2010-181391 A    8/2010
WO   2017/073737 A1   5/2017

OTHER PUBLICATIONS

PCT, International Search Report for the corresponding application No. PCT/JP2018/045591, dated Mar. 5, 2019, with English translation.
(Continued)

*Primary Examiner* — Md M Rahman
(74) *Attorney, Agent, or Firm* — Lucas & Mercanti, LLP

(57) ABSTRACT

In a method of determining the type of each cell contained in a sample, one Raman spectrum is acquired from one undetermined cell, a plurality of degrees of matching of a Raman spectrum of the undetermined cell with respect to spectra of a plurality of principal components obtained by principal component analysis of a plurality of Raman spectra that are obtained one by one from each of a plurality of known types of cells are calculated, and a type of the undetermined cell is determined by classifying the plurality of degrees of matching based on a result obtained by classifying a plurality of principal component scores corresponding to each of the plurality of known types of cells obtained by the principal component analysis depending on the type of cells by a learning model using supervised learning.

9 Claims, 15 Drawing Sheets

(58) Field of Classification Search
USPC .......................................................... 356/301
See application file for complete search history.

(56) References Cited

OTHER PUBLICATIONS

Kim W, et al., "Instrument-Free Synthesizable Fabrication of Label-Free Optical Biosensing Paper Strips for the Early Detection of Infectious Keratoconjunctivitides," Analytical Chemistry, Apr. 29, 2016, pp. 5531-5537, vol. 88, ACS Publications.

Dies H., et al., "Rapid identification and quantification of illicit drugs on nanodendritic surface-enhanced Raman scattering substrates," Sensors and Actuators B: Chemical, 2018, pp. 382-388, vol. 257, Elsevier.

F I G. 1
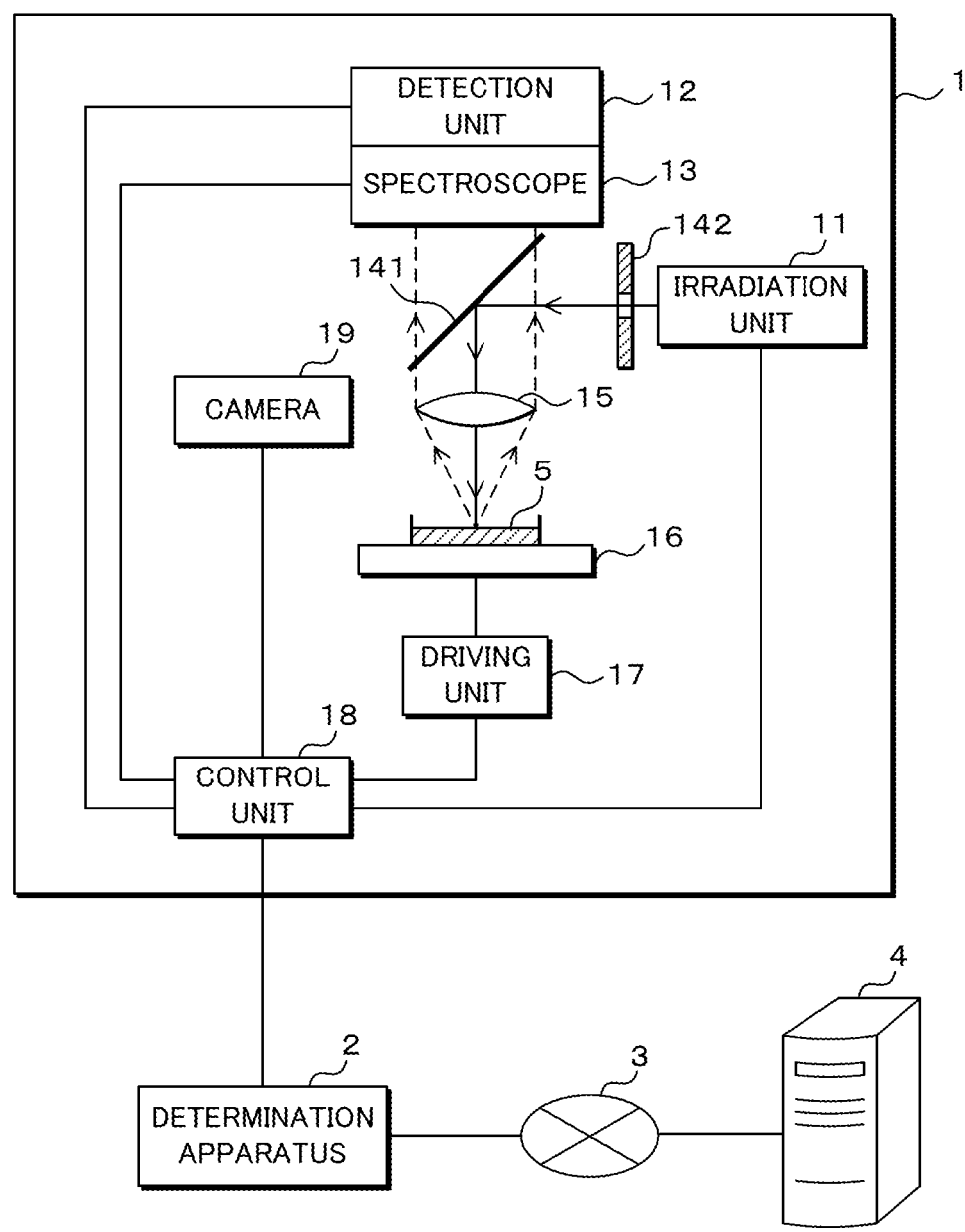

FIG. 5

| | RAMAN SHIFT(cm$^{-1}$) | | | | | | |
|---|---|---|---|---|---|---|---|
| CELL NUMBER | 1253.871 | 1257.133 | 1260.424 | 1263.714 | ... | 3047.522 | 3050.176 |
| 1 | ✳ ✳ | ✳ ✳ | ✳ ✳ | ✳ ✳ | ... | ✳ ✳ | ✳ ✳ |
| 2 | ✳ ✳ | ✳ ✳ | ✳ ✳ | ✳ ✳ | ... | ✳ ✳ | ✳ ✳ |
| 3 | ✳ ✳ | ✳ ✳ | ✳ ✳ | ✳ ✳ | ... | ✳ ✳ | ✳ ✳ |
| ⋮ | ⋮ | ⋮ | ⋮ | ⋮ | ⋮ | ⋮ | ⋮ |
| N | ✳ ✳ | ✳ ✳ | ✳ ✳ | ✳ ✳ | ... | ✳ ✳ | ✳ ✳ |

F I G. 6A
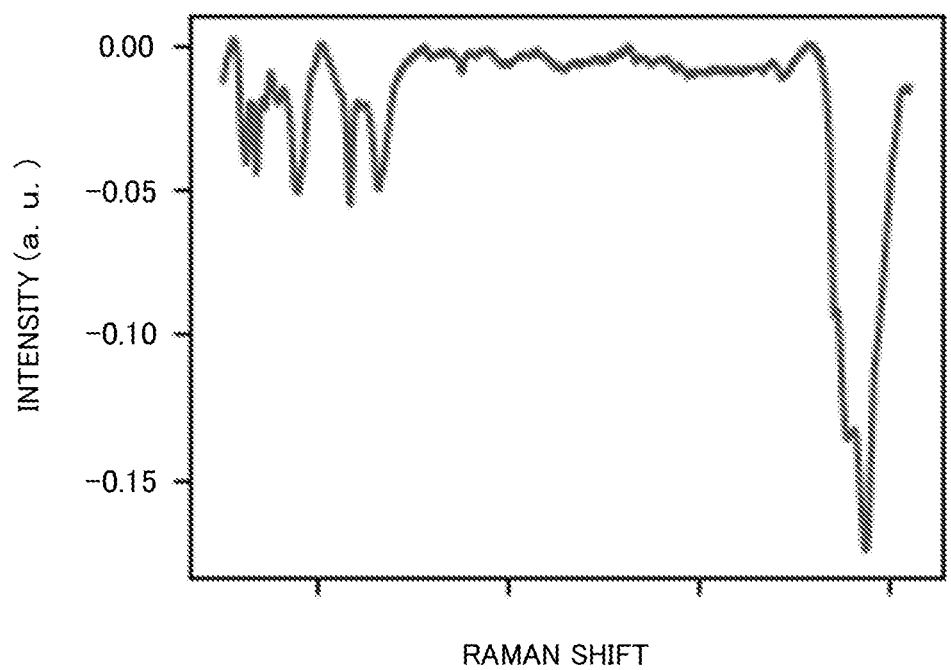
F I G. 6B
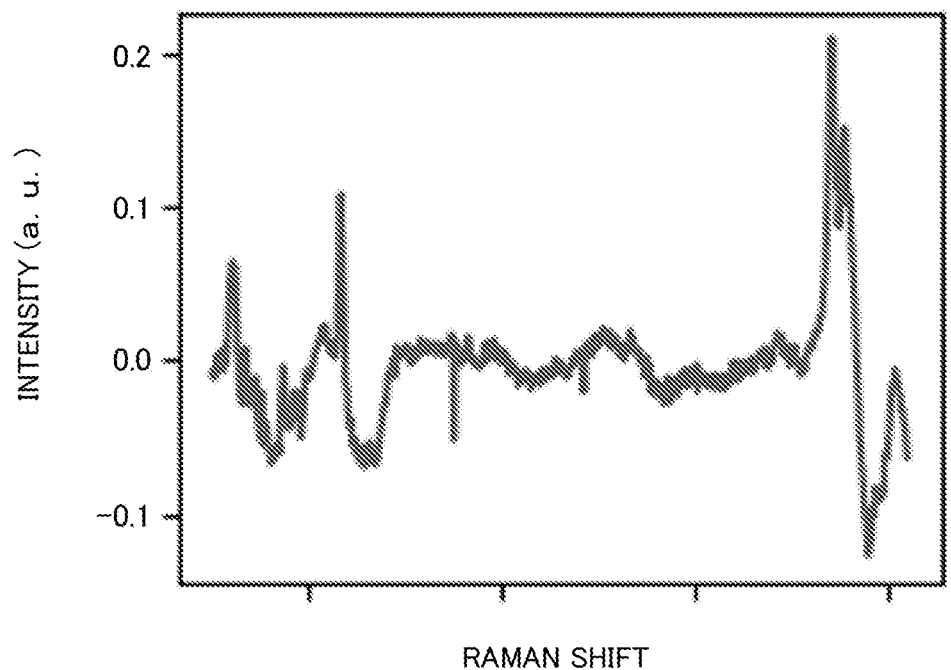

F I G. 7

| CELL NUMBER | FIRST PRINCIPAL COMPONENT SCORE | SECOND PRINCIPAL COMPONENT SCORE | THIRD PRINCIPAL COMPONENT SCORE | ... |
|---|---|---|---|---|
| 1 | ** | ** | ** | ... |
| 2 | ** | ** | ** | ... |
| 3 | ** | ** | ** | ... |
| ⋮ | ⋮ | ⋮ | ⋮ | ⋮ |
| N | ** | ** | ** | ... |

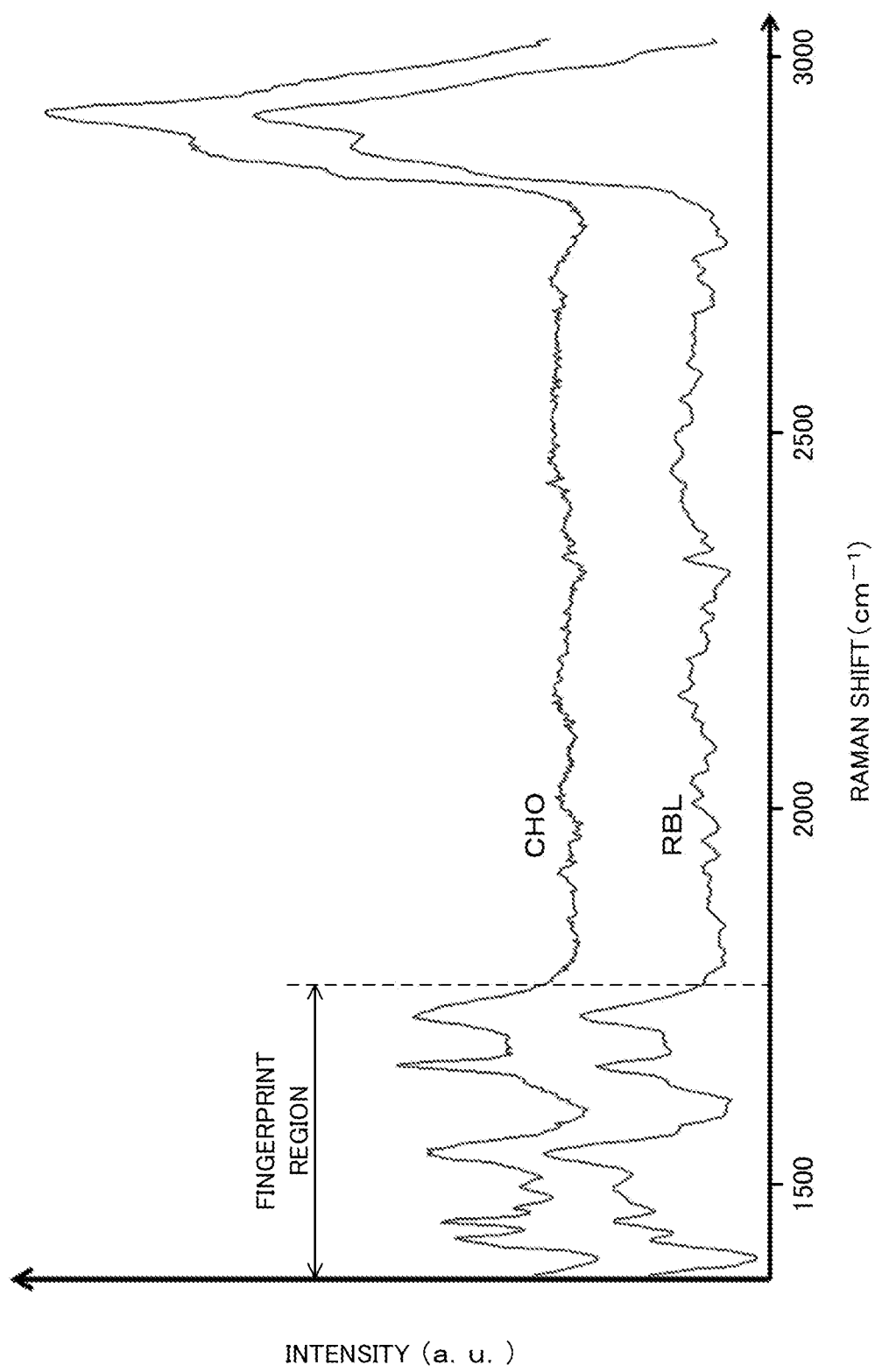

F I G. 1 4 A
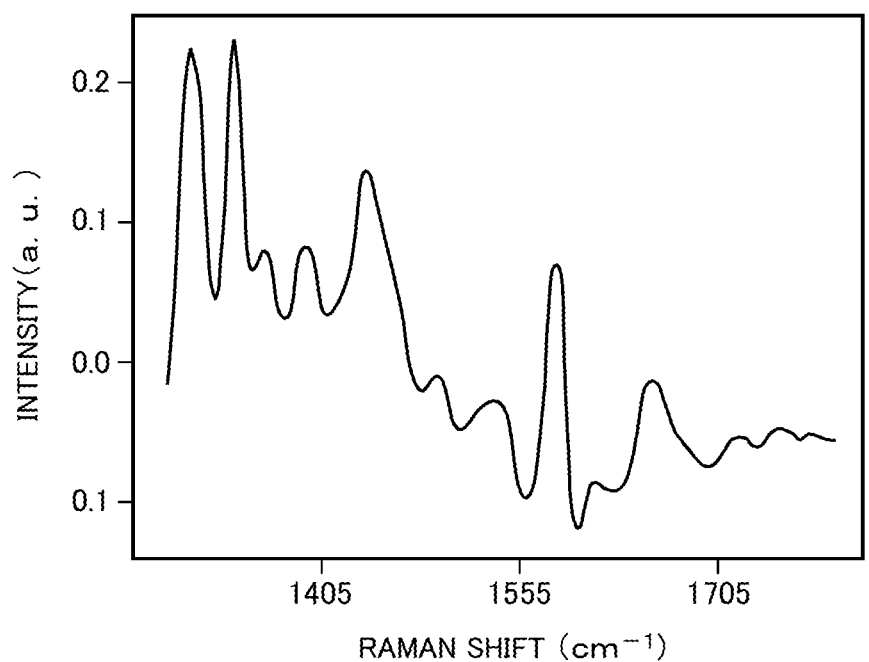
F I G. 1 4 B
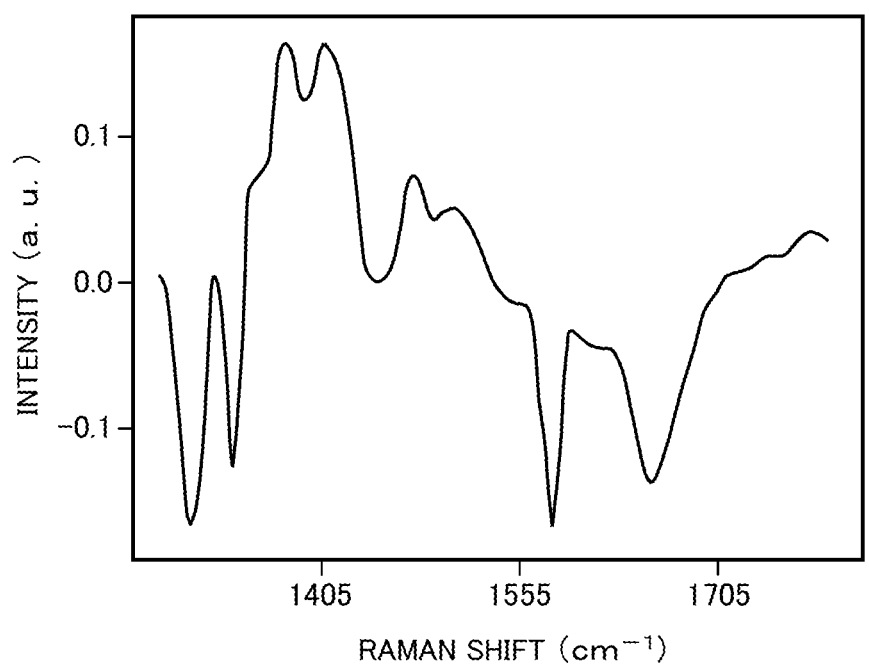

DETERMINATION METHOD, DETERMINATION APPARATUS, AND RECORDING MEDIUM

CROSS REFERENCE TO RELATED APPLICATION

This Application is a 371 of PCT/JP2018/045591 filed on Dec. 12, 2018 which, in turn, claimed the priority of Japanese Patent Application No. 2017-238644 filed on Dec. 13, 2017, both applications are incorporated herein by reference.

FIELD

The present invention relates to a determination method, a determination apparatus, and a recording medium for determining a cell type based on a Raman spectrum.

BACKGROUND

In the field of regenerative medicine, it is necessary to examine whether or not cultured cells have differentiated into desired types of cells. In the field of medical diagnosis, it is sometimes necessary to determine whether or not cells collected from a patient are normal types of cells. Thus, a method for determining the type of each cell derived from an organism is required. In the case of using a method of staining cells or a method of destroying cells, it is not possible to observe the time-series changes of determined cells or to culture the determined cells. For this reason, it is desirable that the method of determining the cell type is a non-destructive and non-invasive method.

As such a method, there is a method using Raman spectroscopy. Japanese Patent Laid-Open Publication No. 2010-181391 describes that principal component analysis is performed on a Raman spectrum measured from a plurality of locations of a cell or a Raman spectrum in a predetermined wavelength range and the cell is determined from the obtained principal component score.

SUMMARY

When measuring the Raman scattered light from a cell, the Raman scattered light is generated from each portion in the cell, such as a cell membrane, a nucleus, and a Golgi body. For this reason, the Raman spectrum obtained from the cell has a complicated shape due to the superposition of a large number of signals. Therefore, it is difficult to find out a Raman band characterizing the cell from the Raman spectrum obtained from the cell and evaluate the Raman band. The technique described in Japanese Patent Laid-Open Publication No. 2010-181391 has a problem that the time required for measurement is long since it is necessary to obtain the distribution of the Raman spectrum in the cell. In addition, even in cells of the same type, the distribution of various structures within the cells is diverse. Accordingly, the importance of obtaining the distribution of the Raman spectrum depending on the distribution of the structures is not clear. In other words, a method of accurately determining the cell type using the Raman spectrum has not been established yet.

The present disclosure has been made in view of such circumstances, and it is an object to provide a determination method, a determination apparatus, and a recording medium capable of determining a cell type based on a Raman spectrum obtained from a cell more accurately than before.

A determination method of determining a type of each cell contained in a sample, according to an aspect of the present disclosure, comprises: acquiring one Raman spectrum from one undetermined cell; calculating a plurality of degrees of matching of a Raman spectrum of the undetermined cell with respect to spectra of a plurality of principal components obtained by principal component analysis of a plurality of Raman spectra that are obtained one by one from each of a plurality of known types of cells; and determining a type of the undetermined cell by classifying the plurality of degrees of matching, based on a result obtained by classifying a plurality of principal component scores corresponding to each of the plurality of known types of cells obtained by the principal component analysis depending on the type of cells by a learning model using supervised learning.

In the determination method according to an aspect of the present disclosure, the learning model is a support vector machine.

In the determination method according to an aspect of the present disclosure, the machine learning of the learning model is performed using, as training data, the plurality of principal component scores corresponding to each of the plurality of known types of cells and each of the types of the plurality of cells.

In the determination method according to an aspect of the present disclosure, one entire cell is irradiated with excitation light, and a Raman spectrum is acquired by measuring Raman scattered light from the one entire cell.

A learning method of learning for determining a type of each cell contained in a sample based on a Raman spectrum, according to an aspect of the present disclosure, comprises: acquiring spectra of a plurality of principal components, which are obtained by principal component analysis of a plurality of Raman spectra that are obtained one by one from each of a plurality of known types of cells, and a plurality of principal component scores corresponding to each of the plurality of cells; performing machine learning of a learning model so that a plurality of sets of the plurality of principal component scores are able to be classified depending on the type of the plurality of cells by the learning model using supervised learning with, as training data, the plurality of sets of the plurality of principal component scores and each of the types of the plurality of cells; and storing the spectra of the plurality of principal components and a result of classification of the plurality of principal component scores by the learning model after learning.

In the learning method according to an aspect of the present disclosure, the plurality of sets of the plurality of principal component scores are classified by dividing a coordinate space, in which a plurality of coordinate points having the plurality of principal component scores as coordinate components are included, into a plurality of regions by the learning model.

A determination apparatus for determining a type of each cell contained in a sample, according to an aspect of the present disclosure, comprises: a calculation unit that calculates a plurality of degrees of matching of a Raman spectrum acquired from an undetermined cell with respect to spectra of a plurality of principal components obtained by principal component analysis of a plurality of Raman spectra that are obtained one by one from each of a plurality of known types of cells; and a determination unit that determines a type of the undetermined cell by classifying the plurality of degrees of matching based on a result obtained by classifying a plurality of principal component scores corresponding to each of the plurality of known types of cells obtained by the principal component analysis depending on the type of cells by a learning model using supervised learning.

The determination apparatus according to an aspect of the present disclosure further comprises a learning unit that performs machine learning of the learning model using, as training data, the plurality of principal component scores corresponding to each of the plurality of known types of cells and each of the types of the plurality of cells.

The determination apparatus according to an aspect of the present disclosure further comprises a first acquisition unit that acquires the training data from outside.

The determination apparatus according to an aspect of the present disclosure further comprises a second acquisition unit that acquires, from outside, the spectra of the plurality of principal components and a result, which is obtained by classifying the plurality of principal component scores corresponding to each of the plurality of known types of cells depending on the type of cells by the learning model.

A computer program for causing a computer to execute a process for determining a type of each cell contained in a sample, according to an aspect of the present disclosure, causes the computer to execute a process including: a step of calculating a plurality of degrees of matching indicating a degree of contribution of a Raman spectrum acquired from an undetermined cell to spectra of a plurality of principal components obtained by principal component analysis of a plurality of Raman spectra that are obtained one by one from each of a plurality of known types of cells; and a step of determining a type of the undetermined cell by classifying the plurality of degrees of matching, based on a result obtained by classifying a plurality of principal component scores corresponding to each of the plurality of known types of cells obtained by the principal component analysis depending on the type of cells by a learning model using supervised learning.

A computer program for causing a computer to perform learning for determining a type of each cell contained in a sample, according to an aspect of the present disclosure, causes the computer to execute a process including: a step of acquiring spectra of a plurality of principal components, which are obtained by principal component analysis of a plurality of Raman spectra that are obtained one by one from each of a plurality of known types of cells, and a plurality of principal component scores corresponding to each of the plurality of cells; a step of performing machine learning of a learning model so that the plurality of principal component scores are able to be classified depending on the type of the plurality of cells by the learning model using supervised learning with, as training data, a plurality of sets of the plurality of principal component scores and each of the types of the plurality of cells; and a step of storing the spectra of the plurality of principal components and a result of classification of the plurality of principal component scores by the learning model after learning.

In an aspect of the present disclosure, one Raman spectrum is acquired from one cell, and the type of the cell is determined based on the acquired Raman spectrum. In addition, based on the result of the principal component analysis of the plurality of Raman spectra obtained from the plurality of known types of cells, a plurality of degrees of matching indicating the degree of matching of the Raman spectrum of the undetermined cell with respect to the spectrum of the principal component are calculated. By classifying the plurality of degrees of matching corresponding to the undetermined cell based on the result obtained by classifying the plurality of principal component scores corresponding to the plurality of known types of cells by the learning model using supervised learning, the type of the cell is determined. By using the Raman spectrum obtained one by one from each cell, processing for determination according to the characteristics of the entire cell can be performed. In addition, the determination may be performed using the entire Raman spectrum, or the determination may be performed using a part of the Raman spectrum without using the other part. In addition, the learning may be performed using the entire Raman spectrum, or the learning may be performed using a part of the Raman spectrum without using the other part.

In addition, in an aspect of the present disclosure, by using the support vector machine as a learning model using supervised learning, a plurality of principal component scores corresponding to each of a plurality of cells can be easily classified, and a plurality of degrees of matching corresponding to the undetermined cell can be easily classified.

In an aspect of the present disclosure, machine learning of a learning model, such as a support vector machine, is performed using, as training data, a plurality of principal component scores corresponding to each of a plurality of known types of cells and the type of each cell. As a result of machine learning, it is possible to determine the cell type more accurately.

In addition, in an aspect of the present disclosure, the determination apparatus for determining the cell type acquires the training data from the outside. The learning model can be learned based on the result of the Raman spectrum measurement performed by a person other than the user of the determination apparatus.

In addition, in an aspect of the present disclosure, the determination apparatus acquires, from the outside, the spectra of the plurality of principal components, which are obtained by principal component analysis of the plurality of Raman spectra obtained from the plurality of known types of cells, and the result obtained by classifying the plurality of principal component scores corresponding to each of the plurality of known types of cells according to types using a learning model. The cell type can be determined using the result of learning performed by a person other than the user of the determination apparatus.

In addition, in an aspect of the present disclosure, when classifying the plurality of principal component scores corresponding to each of the plurality of known types of cells, the coordinate space including coordinate points having a plurality of principal component scores as coordinate components is divided into a plurality of regions by a learning model, such as a support vector machine. For example, the coordinate points are two-dimensional coordinate points having a first principal component score and a second principal component score as coordinate components. According to the division of the coordinate space, the plurality of principal component scores are classified by cell types.

In addition, in an aspect of the present disclosure, when acquiring one Raman spectrum from one cell, excitation light is emitted to one entire cell, and the Raman scattered light from the one entire cell is measured. The measurement of the Raman spectrum can be performed in a short time, and the measurement of the Raman spectrum reflecting the characteristics of the entire cell can be performed.

In an aspect of the present disclosure, processing for determination according to the characteristics of the entire cell is performed without being affected by the detailed structure in the cell, and the cell type is determined by comparing the overall characteristics of the Raman spectrum instead of using some Raman bands included in the Raman spectrum. Therefore, an aspect of the present disclosure has an excellent effect, for example, it is possible to determine the cell type more accurately than before.

The above and further objects and features will more fully be apparent from the following detailed description with accompanying drawings.

BRIEF DESCRIPTION OF THE DRAWINGS

FIG. 1 is a block diagram illustrating the configuration of a Raman scattered light measuring apparatus;

FIG. 5 is a table showing an example of Raman spectrum data;

FIG. 6A is a graph showing an example of the spectrum of each principal component obtained by performing principal component analysis of a plurality of Raman spectra obtained from a plurality of RBLs and a plurality of CHOs;

FIG. 6B is a graph showing an example of the spectrum of each principal component obtained by performing principal component analysis of a plurality of Raman spectra obtained from a plurality of RBLs and a plurality of CHOs;

FIG. 7 is a table showing an example of a result of calculation of a principal component score;

FIG. 13 is a graph showing an example of a fingerprint region in the Raman spectra;

FIG. 14A is a graph showing an example of the spectrum of a principal component relevant to a fingerprint region;

FIG. 14B is a graph showing an example of the spectrum of a principal component relevant to a fingerprint region.

DETAILED DESCRIPTION

Figure 2:
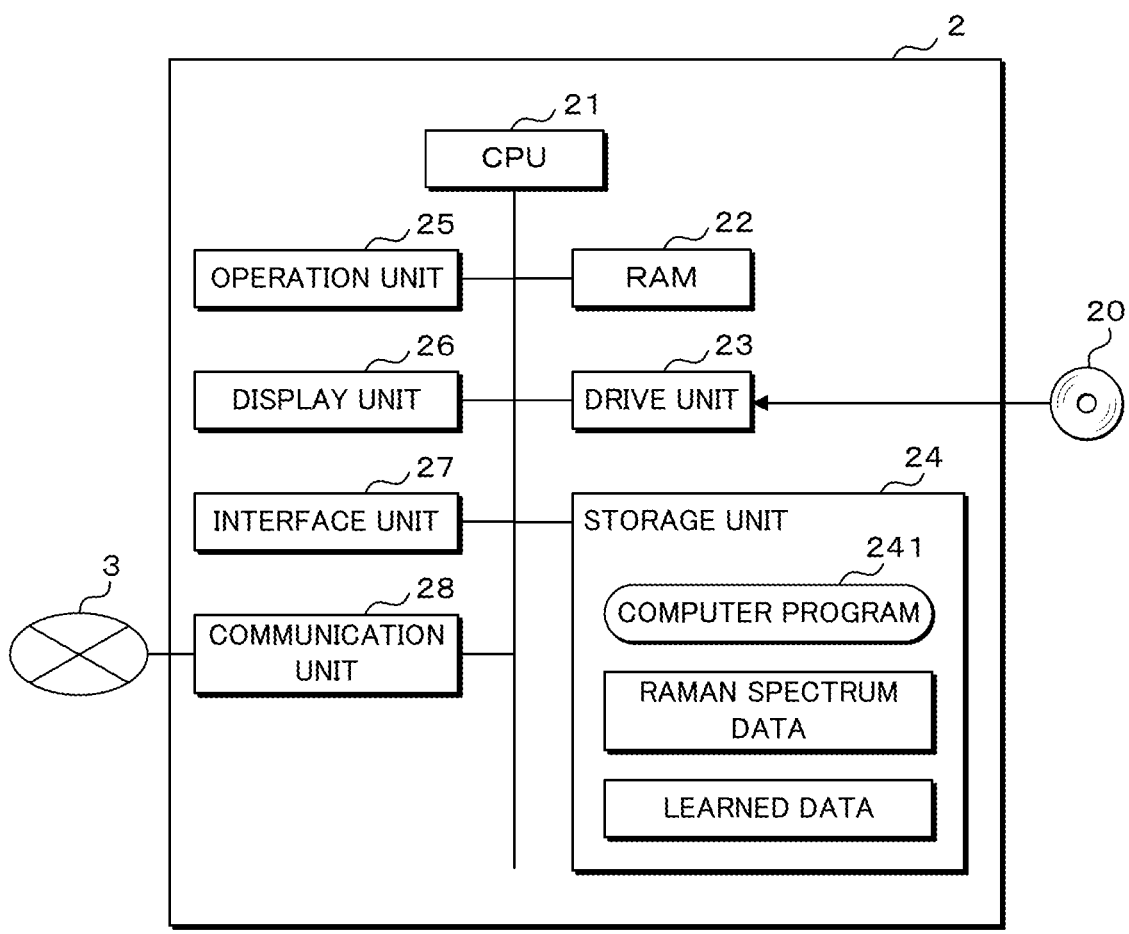
FIG. 2 is a block diagram illustrating the internal configuration of a determination apparatus.

Hereinafter, the present disclosure will be specifically described with reference to the diagrams showing the embodiments.

In a cell type determination method according to the present embodiment, a Raman scattered light measuring apparatus measures the Raman spectrum of each cell from a sample containing a plurality of cells, and a determination apparatus determines the cell type based on the measured Raman spectrum. The sample contains a plurality of types of cells. For example, the sample is a sample containing cultured cells or a sample containing cells collected from an organism, such as a human. Here, the difference in cell type refers to a difference between an activated cell and a non-activated cell, a difference between a live cell and a dead cell, a difference between a normal cell and an abnormal cell, and the like.

First Embodiment

FIG. 1 is a block diagram illustrating the configuration of a Raman scattered light measuring apparatus 1. The Raman scattered light measuring apparatus 1 includes a sample holding unit 16 for holding a sample 5, an irradiation unit 11 for emitting laser light, a mask 142, a beam splitter 141, and a lens 15. For example, the sample 5 is in a liquid state and stored in a container such as a petri dish. The sample holding unit 16 is, for example, a sample table on which a container containing the sample 5 is placed. The sample holding unit 16 may be in a form other than the sample stage. The laser light emitted from the irradiation unit 11 is focused into thin light by the mask 142, reflected by the beam splitter 141, passes through the lens 15, and is irradiated to the sample 5. The irradiation unit 11, the mask 142, the beam splitter 141, and the lens 15 are disposed so that the laser light passes only through the optical axis and the vicinity of the optical axis in the lens 15. In FIG. 1, the laser light is indicated by solid arrows.

The Raman scattered light measuring apparatus 1 further includes a spectroscope 13 and a detection unit 12 that detects light. Raman scattering occurs in a portion of the sample 5 irradiated with the laser light. The generated Raman scattered light is condensed by the lens 15, passes through the beam splitter 141, and is incident into the spectroscope 13. In FIG. 1, the Raman scattered light is indicated by broken arrows. The spectroscope 13 disperses the incident Raman scattered light. The detection unit 12 detects the light of each wavelength that is dispersed by the spectroscope 13. The Raman scattered light measuring apparatus 1 includes an optical system including a large number of optical components such as a mirror, a lens, and a filter for guiding, condensing, and separating laser light and Raman scattered light. In FIG. 1, optical components other than the mask 142, the lens 15, and the beam splitter 141 are omitted. In addition, the Raman scattered light measuring apparatus 1 may have a configuration in which the laser light from the irradiation unit 11 passes through the beam splitter 141 and the Raman scattered light is reflected by the beam splitter 141.

The Raman scattered light measuring apparatus 1 further includes a driving unit 17 for moving the sample holding unit 16, a control unit 18, and a camera 19 for observing the sample 5 held by the sample holding unit 16. For example, the driving unit 17 moves the sample holding unit 16 in the horizontal direction. Due to the movement of the sample holding unit 16 by the driving unit 17, the sample 5 moves, and a portion of the sample 5 irradiated with the laser light from the irradiation unit 11 is changed. That is, by the operation of the driving unit 17, a portion where Raman scattered light is generated in the sample 5 is changed. The camera 19 includes, for example, an imaging device. The irradiation unit 11, the detection unit 12, the spectroscope 13, the driving unit 17, and the camera 19 are connected to the control unit 18.

The control unit 18 controls each unit of the Raman scattered light measuring apparatus 1. The irradiation unit 11 is controlled on and off by the control unit 18. The wavelength of light detected by the detection unit 12 after being dispersed by the spectroscope 13 is controlled by the control unit 18. The detection unit 12 outputs a signal corresponding to the detection intensity of the light of each wavelength to the control unit 18. The control unit 18 receives the signal output from the detection unit 12, and generates a Raman spectrum based on the wavelength of the light dispersed by the spectroscope 13 and the detection intensity of the light indicated by the input signal. The control unit 18 controls the operation of the driving unit 17 to move the sample holding unit 16 and change a portion where Raman scattered light is generated in the sample 5. In addition, the control unit 18 causes the camera 19 to take an image of the sample 5, so that a portion where Raman scattered light is generated in the sample 5 can be checked. In this manner, the Raman scattered light measuring apparatus 1 can acquire the Raman spectrum from each portion of the sample 5. For example, the camera 19 is disposed so as to take an image of the sample 5 using light on the same axis as the laser light emitted from the irradiation unit 11 to the sample 5. By performing taking the image using the light on the same axis as the laser light, it becomes easy to check and adjust the position of a portion where Raman scattered light is generated in the sample 5.

A determination apparatus 2 that performs processing for determining the type of each cell contained in the sample 5 is connected to the Raman scattered light measuring apparatus 1. The determination apparatus 2 is connected to the control unit 18. FIG. 2 is a block diagram illustrating the internal configuration of the determination apparatus 2. The determination apparatus 2 is configured using a computer, such as a personal computer. The determination apparatus 2 includes a central processing unit (CPU) 21 for performing calculation, a random access memory (RAM) 22 for storing temporary data generated by the calculation, a drive unit 23 for reading information from a recording medium 20 such as an optical disk, and a non-volatile storage unit 24 such as a hard disk. In addition, the determination apparatus 2 includes an operation unit 25 such as a keyboard or a mouse for receiving a user's operation, a display unit 26 such as a liquid crystal display, an interface unit 27, and a communication unit 28. The control unit 18 is connected to the interface unit 27. The communication unit 28 is connected to a communication network 3 outside the determination apparatus 2, and communicates with an external apparatus through the communication network 3. The communication unit 28 can download data from the outside through the communication network 3.

The CPU 21 causes the drive unit 23 to read a computer program 241 recorded on the recording medium 20, and stores the read computer program 241 in the storage unit 24. The CPU 21 loads the computer program 241 from the storage unit 24 to the RAM 22 as necessary, and performs processing necessary for the determination apparatus 2 according to the loaded computer program 241. In addition, the computer program 241 may be downloaded from the outside of the determination apparatus 2 through the communication unit 28. The control unit 18 outputs Raman spectrum data representing the generated Raman spectrum to the determination apparatus 2. The determination apparatus 2 receives the Raman spectrum data at the interface unit 27, and the CPU 21 stores the Raman spectrum data in the storage unit 24.

The Raman scattered light measuring apparatus 1 and the determination apparatus 2 configure one analyzer. The determination apparatus 2 can also control the operation of the Raman scattered light measuring apparatus 1. The control unit 18 may output image data representing an image of the sample 5 captured by using the camera 19 to the determination apparatus 2, the determination apparatus 2 may receive the image data at the interface unit 27, and the CPU 21 may display the image of the sample 5 represented by the image data on the display unit 26. The user may operate the operation unit 25 to input an instruction for controlling the Raman scattered light measuring apparatus 1. For example, the CPU 21 outputs a control signal, which is for giving an instruction to measure the Raman spectrum of a specific portion in the sample 5, from the interface unit 27 to the control unit 18 according to the input instruction. The control unit 18 receives the control signal, controls the operations of the irradiation unit 11, the detection unit 12, the spectroscope 13, and the driving unit 17 according to the received control signal, and measures the Raman spectrum of a specific portion in the sample 5.

Figure 3:
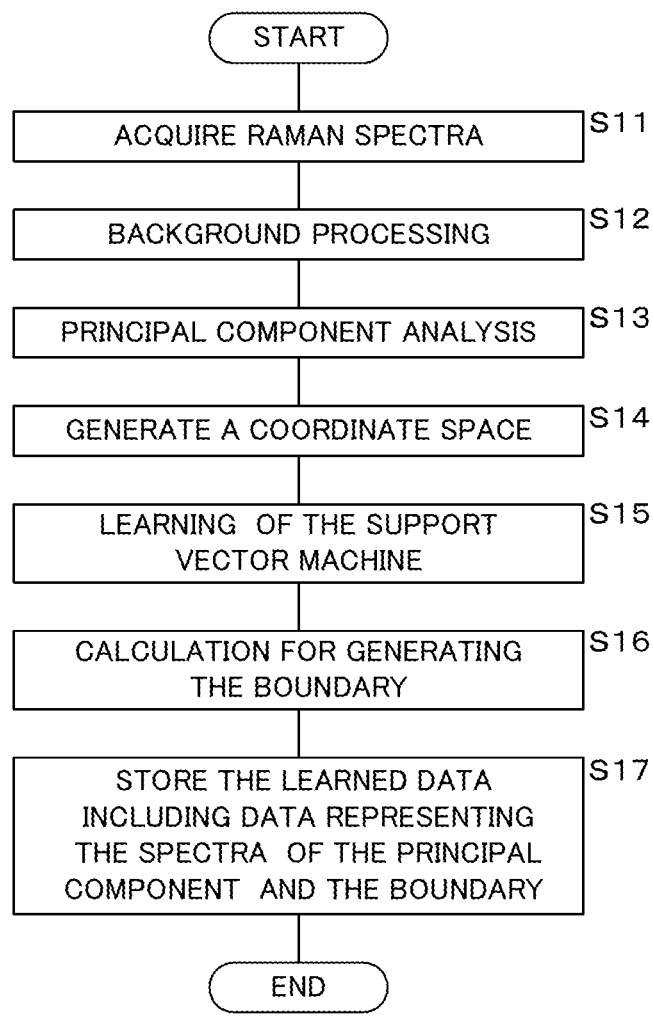
FIG. 3 is a flowchart illustrating the procedure of a process in which a determination apparatus performs learning.

In the present embodiment, the determination apparatus 2 determines a cell type by a support vector machine that is a learning model using supervised learning. In order to appropriately determine the cell type, it is necessary to perform the learning of the support vector machine. FIG. 3 is a flowchart illustrating the procedure of a process in which the determination apparatus 2 performs learning. The CPU 21 performs processing necessary for the determination apparatus 2 according to the computer program 241. The Raman scattered light measuring apparatus 1 acquires a plurality of Raman spectra from the sample 5 containing a plurality of known types of cells (S11). The Raman scattered light measuring apparatus 1 measures the Raman spectra one by one from each of the plurality of cells contained in the sample 5. For example, an optical system including the lens 15 is adjusted so that the laser light from the irradiation unit 11 is emitted to one entire cell, and the Raman scattered light measuring apparatus 1 irradiates the one entire cell with the laser light. The laser light passes through only the optical axis and the vicinity of the optical axis in the lens 15 to be emitted to the one entire cell. The lens 15 collects Raman scattered light generated from the entire cell by irradiation with the laser light, and the detection unit 12 detects Raman scattered light from the entire cell. An average Raman spectrum is obtained for one cell, and the obtained Raman spectrum reflects the characteristics of the entire cell. Since one Raman spectrum is acquired from one cell, the measurement time is shortened as compared with a case where a plurality of Raman spectra are acquired from one cell.

The Raman scattered light measuring apparatus 1 acquires the Raman spectra one by one from each of the plurality of cells while changing cells irradiated with the laser light, by moving the sample holding unit 16 with the driving unit 17. For example, the control unit 18 detects each cell using the camera 19, and controls the driving unit 17 so that the laser light is sequentially emitted to each cell. In addition, for example, the user who has sighted the image of the sample 5 displayed on the display unit 26 may operate the operation unit 25 to input an instruction to change the position of the sample 5 to the determination apparatus 2. A control signal according to the instruction is input from the determination apparatus 2 to the control unit 18, and the control unit 18 controls the driving unit 17 according to the control signal so that the laser light is sequentially emitted to each cell. In this manner, a plurality of Raman spectra are acquired from the sample 5.

Figure 4:
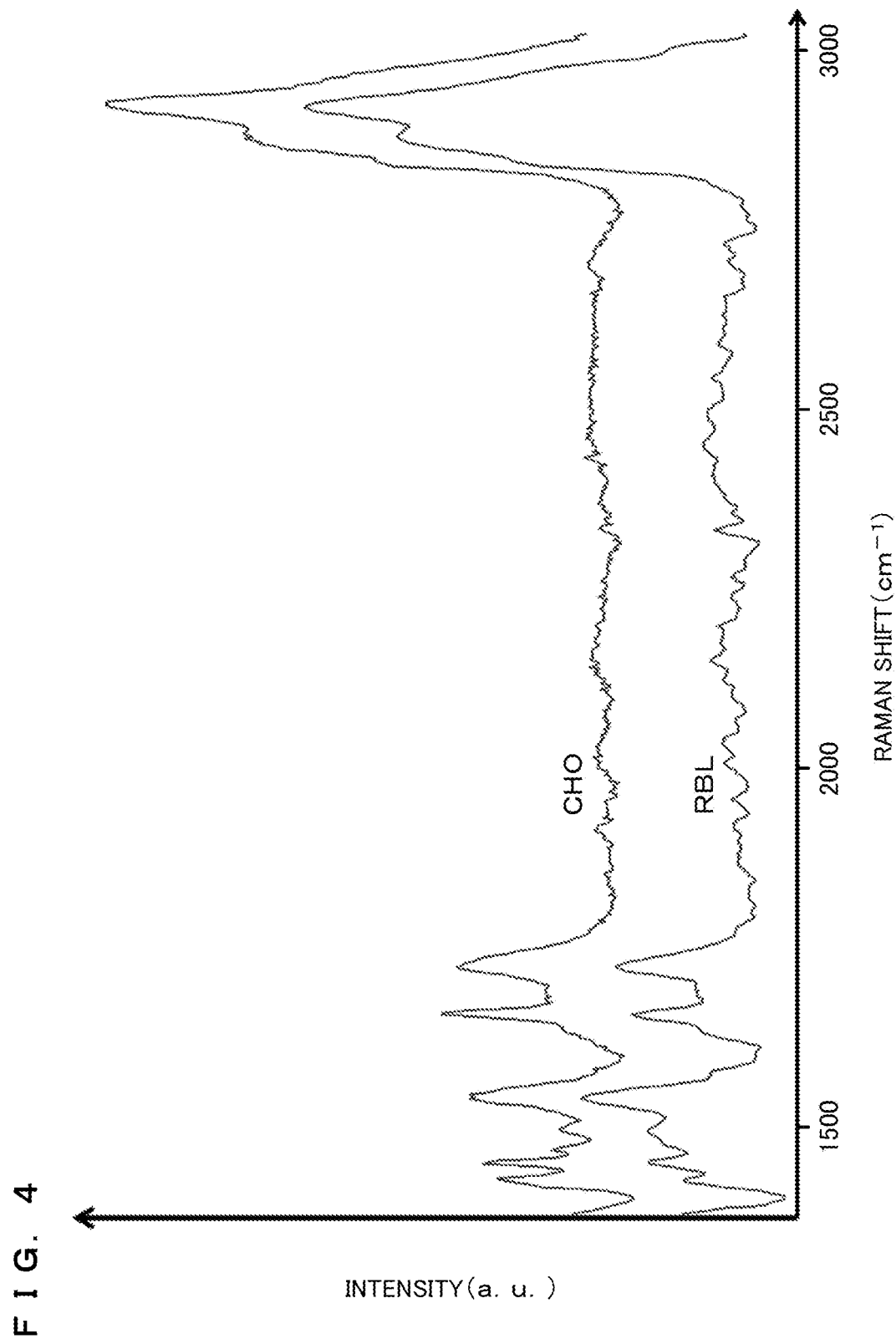
FIG. 4 is a graph showing an example of Raman spectra.

FIG. 4 is a graph showing an example of Raman spectra. The horizontal axis indicates a Raman shift, and the vertical axis indicates the intensity of Raman scattered light at each Raman shift. The Raman shift is expressed by wave number, and the unit is $cm^{-1}$. The unit of the intensity of the Raman scattered light is arbitrary unit (a. u.). FIG. 4 shows an example in which a rat basophilic leukemia cell (RBL) and a Chinese hamster ovary cell (CHO) are used as cells. FIG. 4 shows two types of Raman spectra, with the baseline of the Raman spectrum of the CHO being a value larger than the baseline of the RBL. The shapes of the two types of Raman spectra are similar, and it is difficult to distinguish the two types of cells from the shapes of the Raman spectra.

The control unit 18 outputs Raman spectrum data indicating a plurality of Raman spectra, and the determination apparatus 2 receives the Raman spectrum data at the interface unit 27 and stores the Raman spectrum data in the storage unit 24. The Raman spectrum data includes data representing the Raman spectrum obtained from each of the plurality of cells. The data indicating one Raman spectrum is associated with one cell in which the measured Raman scattered light is generated, that is, a cell from which the Raman spectrum is generated.

FIG. 5 is a table showing an example of Raman spectrum data. FIG. 5 shows an example in which the number of cells for which the Raman spectrum is measured is N (N is a natural number). In FIG. 5, respective cells are numbered so as to be distinguished from each other, and the cell numbers are arranged in the vertical direction. In the Raman spectrum data, the intensity value of the Raman scattered light measured for each Raman shift is recorded in association with each cell. FIG. 5 includes ** indicating a numerical value. For each cell, a plurality of the intensity values of the Raman scattered light are arranged in the horizontal direction, and each intensity value of the Raman scattered light corresponds to each Raman shift value. In FIG. 5, data indicating the Raman spectrum of the cell with the number 1 is surrounded by a thick frame. The Raman spectrum of one cell is expressed by multidimensional data including the intensity of Raman scattered light for each Raman shift. Raman spectrum data includes a plurality of pieces of multidimensional data corresponding to a plurality of cells.

Then, the CPU 21 performs background processing for removing a background signal from the plurality of acquired Raman spectra (S12). Then, the CPU 21 performs principal component analysis of the plurality of Raman spectra (S13). In S13, the CPU 21 performs principal component analysis of the plurality of pieces of multidimensional data representing a plurality of Raman spectra. Specifically, assuming that the number of cells for which the Raman spectrum is measured is N and the number of intensity values of Raman scattered light included in one Raman spectrum is M (M is a natural number), principal component analysis is performed on a matrix of N rows and M columns having intensity values of Raman scattered light as elements. For example, a matrix surrounded by the frame shown in FIG. 5 is a target of the principal component analysis. Multidimensional data including M elements in one row represent one Raman spectrum, and corresponds to one cell.

The CPU 21 performs calculation for generating spectra of a plurality of principal components, such as a spectrum of the first principal component in which information of the largest ratio among all pieces of information of a plurality of Raman spectra is gathered and a spectrum of the second principal component in which information of the next largest ratio is gathered, by principal component analysis. FIGS. 6A and 6B are graphs showing examples of the spectrum of each principal component obtained by performing principal component analysis of a plurality of Raman spectra obtained from a plurality of RBLs and a plurality of CHOs. FIGS. 6A and 6B show the results of principal component analysis of a plurality of Raman spectra obtained from a plurality of RBLs and a plurality of CHOs. FIG. 6A shows an example of the spectrum of the first principal component, and FIG. 6B shows an example of the spectrum of the second principal component. The horizontal axis indicates a Raman shift, and the vertical axis indicates the intensity of Raman scattered light at each Raman shift.

In S13, the CPU 21 further calculates a plurality of principal component scores for each of the plurality of Raman spectra. The principal component score is a numerical value indicating the contribution ratio of each Raman spectrum to the spectrum of the principal component. The first principal component score indicates the contribution ratio of one Raman spectrum to the spectrum of the first principal component, and the second principal component score indicates the contribution ratio of one Raman spectrum to the spectrum of the second principal component. In other words, the principal component score indicates at which ratio the respective Raman spectra are combined to form the spectrum of the principal component. By adding a plurality of Raman spectra each multiplied by the first principal component score, a spectrum of the first principal component is obtained. The CPU 21 calculates a plurality of principal component scores by matrix calculation. A plurality of principal component scores are calculated for each Raman spectrum. As a result, a plurality of principal component scores are obtained for each Raman spectrum and cell.

FIG. 7 is a table showing an example of a result of calculation of a principal component score. A plurality of principal component scores are recorded in association with the numbers of cells from which the Raman spectra are generated. FIG. 7 includes ** in indicating a numerical value. A plurality of principal component scores are arranged in the horizontal direction for each cell. In FIG. 7, values of a plurality of principal component scores for a cell with the number 1 are surrounded by a thick frame. A set of a plurality of principal component scores corresponds to one Raman spectrum, and corresponds to one cell from which the Raman spectrum is generated. A plurality of sets of a plurality of principal component scores are calculated for a plurality of Raman spectra and a plurality of cells. The CPU 21 stores the plurality of sets of the plurality of principal component scores in the RAM 22 or the storage unit 24.

Then, the CPU 21 generates a coordinate space including coordinate points having a plurality of principal component scores corresponding to each of a plurality of cells as coordinate components (S14). For example, the CPU 21 generates a coordinate space including a plurality of coordinate points corresponding to a plurality of cells by plotting, on the two-dimensional coordinates, a plurality of coordinate points having a first principal component score and a second principal component score as coordinate components. Cell information, which indicates the type of cell for which the Raman spectrum has been measured, is received through the interface unit 27 or the operation unit 25, and then the CPU 21 performs learning of the support vector machine using the received cell information and the plurality of principal component scores for the plurality of cells as training data (S15). In S15, the CPU 21 performs machine learning for adjusting the parameters of the support vector machine so that the plurality of principal component scores for the respective cells can be classified according to the type of each cell indicated by the cell information. For example, in order to determine the cell type, the CPU 21 performs processing for dividing the coordinate space, which includes a plurality of coordinate points having a first principal component score and a second principal component score as coordinate components, into a plurality of regions using a support vector machine. At this time, the CPU 21 adjusts the parameters of the support vector machine so as to divide the coordinate space so that coordinate points corresponding to different types of cells are included in different regions.

Figure 8:
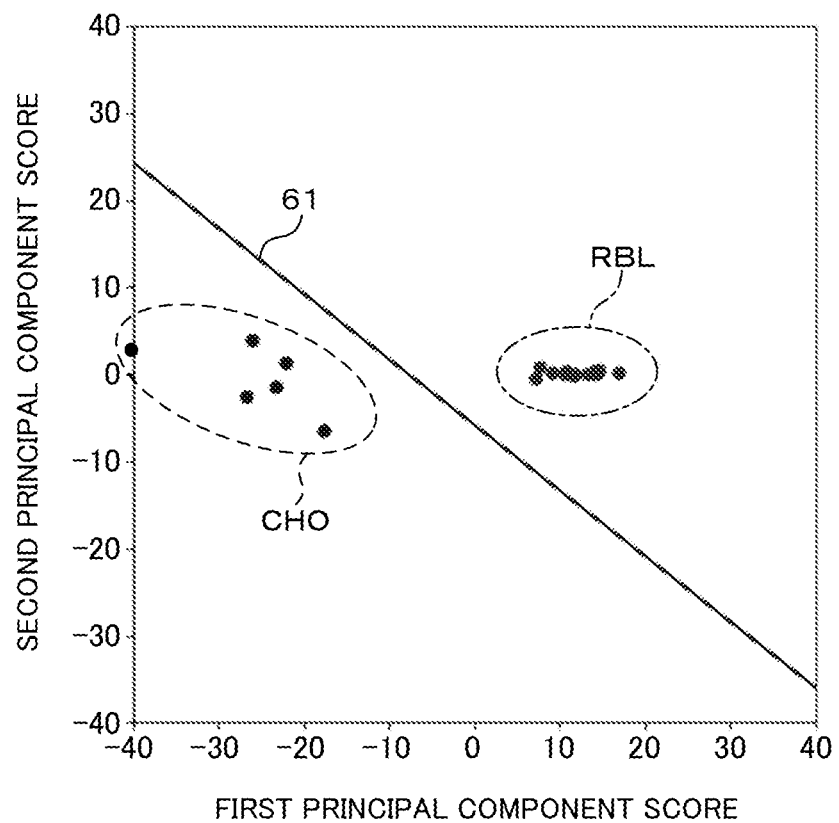
FIG. 8 is a characteristic diagram showing an example in which a coordinate space is divided by a support vector machine according to a first embodiment.

FIG. 8 is a characteristic diagram showing an example in which the coordinate space is divided by the support vector machine according to the first embodiment. In the diagram, the horizontal axis indicates the first principal component score, and the vertical axis indicates the second principal component score. A plurality of coordinate points having a first principal component score and a second principal component score as coordinate components are included in the two-dimensional coordinate space. FIG. 8 shows a plurality of coordinate points corresponding to a plurality of Raman spectra obtained from a plurality of RBLs and a plurality of coordinate points corresponding to a plurality of Raman spectra obtained from a plurality of CHOs. From the same type of cells, Raman spectra having similar shapes are obtained, and the principal component scores are similar numerical values. For this reason, in the coordinate space, coordinate points corresponding to the same type of cells tend to be located close to each other, and coordinate points corresponding to different types of cells tend to be located away from each other. A plurality of coordinate points surrounded by the broken line correspond to a plurality of CHOs. A plurality of coordinate points surrounded by the one-dot chain line correspond to a plurality of RBLs. The CPU 21 adjusts the parameters of the support vector machine so that the dimensional coordinate space can be divided into a region including two-coordinate points corresponding to CHOs and another region including coordinate points corresponding to RBLs by the support vector machine. In FIG. 8, a boundary 61 of the plurality of divided regions is indicated by the straight line. In addition, the CPU 21 adjusts the parameters of the support vector machine so that the margin between the coordinate point and the boundary 61 in the coordinate space is as large as possible. The processing of S15 corresponds to a learning unit.

Then, the CPU 21 performs calculation for generating the boundary 61 by dividing the coordinate space so that the coordinate points corresponding to different types of cells are included in different regions by the processing of the support vector machine after learning (S16). When dividing the two-dimensional coordinate space as shown in FIG. 8, the boundary 61 is generated as a straight line or a curve in the two-dimensional space. Then, the CPU 21 stores the learned data, which indicates the learning result of the support vector machine and includes data representing the spectra of the principal component generated in S13, the boundary 61 generated in S16, and the type of each cell corresponding to each region divided by the boundary 61, in the storage unit 24 (S17). The boundary 61 and the type of each cell corresponding to each region divided by the boundary 61 correspond to a result obtained by classifying a plurality of principal component scores corresponding to each of a plurality of known types of cells according to their types. As described above, the process in which the determination apparatus 2 performs learning is completed. The processing of S11 to S17 is repeated as necessary. For example, the types of cells contained in the sample 5 are changed to repeat the processing of S11 to S17. For example, the processing of S11 to S17 is performed for a combination of a plurality of types that are assumed.

In the above description, an example in which the determination apparatus 2 creates training data is shown. However, the determination apparatus 2 may perform processing for acquiring the training data from the outside. A storage device 4 for storing training data is connected to the communication network 3.

Figure 9:
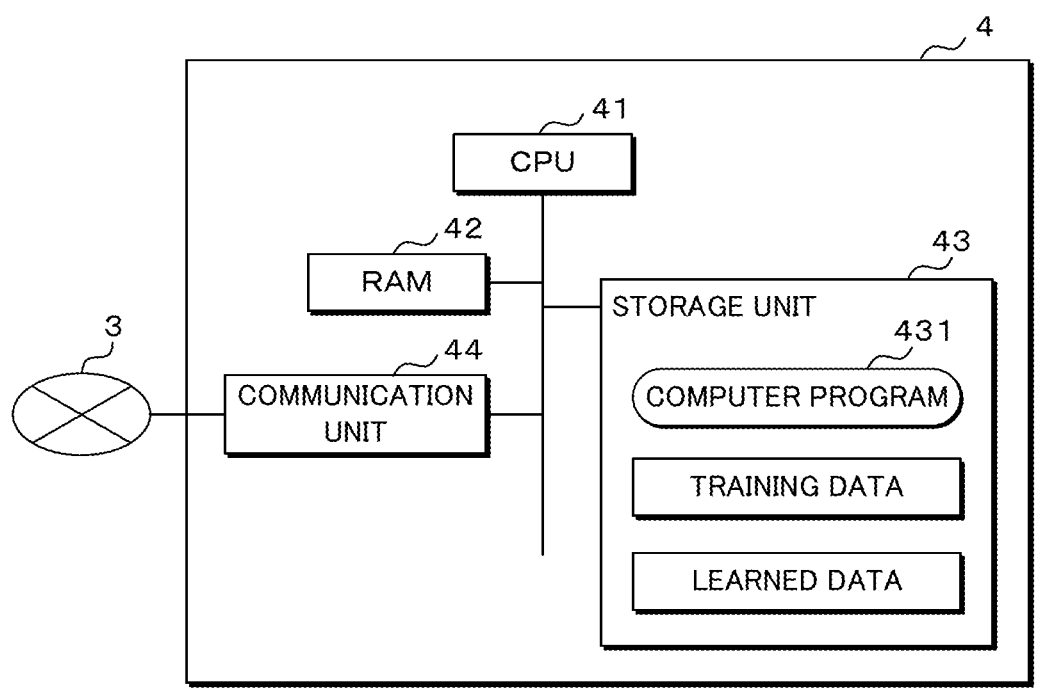
FIG. 9 is a block diagram illustrating an example of the internal configuration of a storage device.

FIG. 9 is a block diagram illustrating an example of the internal configuration of the storage device 4. The storage device 4 is a computer, such as a server apparatus. The storage device 4 includes a CPU 41, a RAM 42, a non-volatile storage unit 43 such as a hard disk, and a communication unit 44. The communication unit 44 is connected to the communication network 3. The storage unit 43 stores a computer program 431. The CPU 41 performs various processes according to the computer program 431. In addition, the storage unit 43 stores training data. The training data is uploaded to the storage device 4 by the maker of the Raman scattered light measuring apparatus 1 or the determination apparatus 2 or by other users. In the present embodiment, an example in which the storage device 4 is configured by a single computer is shown. However, the storage device 4 may be configured by a plurality of computers connected to each other through the communication network 3.

Figure 10:
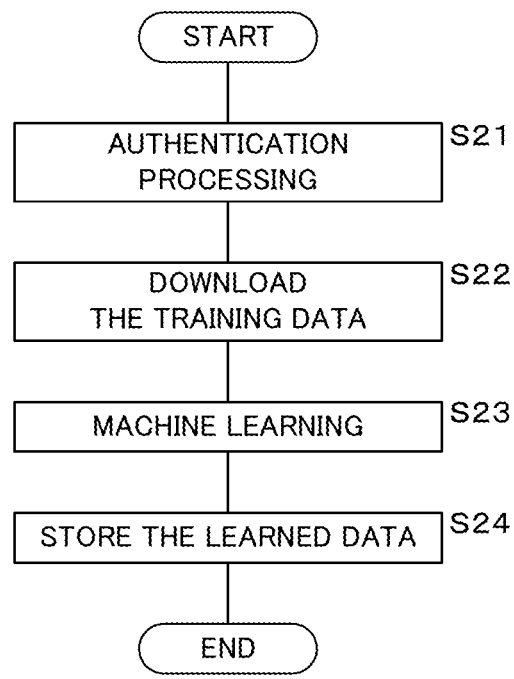
FIG. 10 is a flowchart illustrating the procedure of a process in which training data is acquired from the outside and a determination apparatus performs learning.

FIG. 10 is a flowchart illustrating the procedure of a process in which training data is acquired from the outside and the determination apparatus 2 performs learning. The determination apparatus 2 and the storage device 4 perform authentication processing required for the determination apparatus 2 to acquire the training data from the storage device 4 (S21). For example, the CPU 21 of the determination apparatus 2 causes the communication unit 28 to transmit authentication information, such as a password input by the user operating the operation unit 25, to the storage device 4 through the communication network 3. The CPU 41 of the storage device 4 determines whether or not the authentication information transmitted from the determination apparatus 2 is valid, and performs processing for allowing the download of the training data if the authentication information is valid and disallowing the download if the authentication information is not valid. In addition, for example, the CPU 21 of the determination apparatus 2 performs processing for paying a fee for using the training data. The CPU 41 of the storage device 4 performs processing for checking whether or not the processing for payment has been performed, and performs processing for allowing the download of the training data when it is checked that the processing for payment has been performed and disallowing the download when it is not checked that the processing for payment has been performed. For example, the CPU 41 causes the communication unit 44 to transmit information indicating the authentication result to the determination apparatus 2 through the communication network 3.

When the authentication result that allows the download is obtained, the CPU 21 downloads the training data from the storage device 4 through the communication unit 28 and stores the data in the storage unit 24 (S22). For example, the CPU 21 performs the processing of S22 when the information indicating the authentication result allowing the download is received through the communication unit 28. The training data includes spectra of a plurality of principal components obtained by principal component analysis of Raman spectra of a plurality of cells, a plurality of principal component scores corresponding to each of the plurality of cells, and cell information indicating the type of each cell. The processing of S22 corresponds to a first acquisition unit. The CPU 21 performs machine learning of the support vector machine using the downloaded training data (S23). The processing of S23 is the same processing as the processing of S14 to S16. Then, the CPU 21 stores the learned data, which includes data representing the spectra of the principal component included in the training data, the generated boundary 61, and the type of each cell corresponding to each region, in the storage unit 24 (S24), and ends the process in which the determination apparatus 2 performs learning.

In addition, the determination apparatus 2 may perform processing for acquiring Raman spectrum data from the outside. The storage device 4 stores Raman spectrum data and cell information in the storage unit 43. The Raman spectrum data and the cell information are uploaded to the storage device 4 by the maker of the Raman scattered light measuring apparatus 1 or the determination apparatus 2 or by other users. The CPU 21 acquires the Raman spectrum data from the outside by downloading the Raman spectrum data and the cell information from the storage device 4 through the communication network 3 by the communication unit 28 in S11, and stores the Raman spectrum data and the cell information in the storage unit 24. The CPU 21 performs the processing of S12 to S17 using the acquired Raman spectrum data and cell information. Before performing the download, the CPU 21 may perform the same authentication processing as in S21.

In addition, the training data used for learning may be data obtained from a plurality of measurements. For example, the Raman scattered light measuring apparatus 1 may perform measurement multiple times using a plurality of samples 5, and the determination apparatus 2 may create training data from the Raman spectra obtained by the plurality of measurements. For example, the Raman scattered light measuring apparatus 1 may perform measurement multiple times using a plurality of samples 5 containing different cells, and the determination apparatus 2 may create training data from the Raman spectra obtained by the plurality of measurements. In addition, the training data used for learning may be data including both training data created from Raman spectrum data and training data acquired from the outside.

Figure 11:
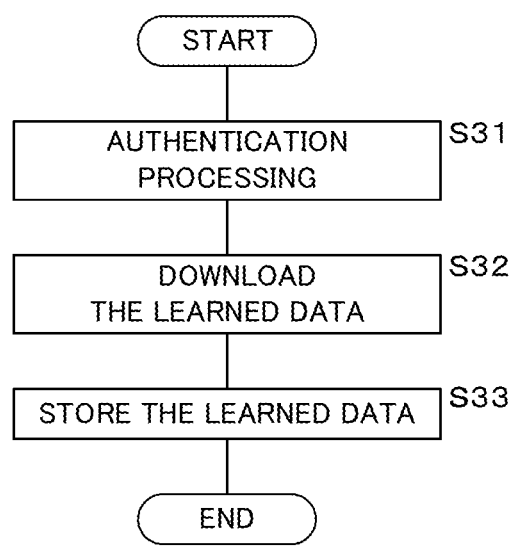
FIG. 11 is a flowchart illustrating the procedure of a process in which a determination apparatus performs learning by acquiring learned data from the outside.

In addition, the determination apparatus 2 may perform processing for acquiring learned data from the outside. The storage device 4 stores, in the storage unit 43, the learned data including data representing the spectra of the principal component, the boundary 61 generated by the support vector machine, and the type of each cell corresponding to each region divided by the boundary 61. The learned data is uploaded to the storage device 4 by the maker of the Raman scattered light measuring apparatus 1 or the determination apparatus 2 or by other users. FIG. 11 is a flowchart illustrating the procedure of a process in which the determination apparatus 2 performs learning by acquiring learned data from the outside. The determination apparatus 2 and the storage device 4 perform authentication processing required for the determination apparatus 2 to acquire the learned data from the storage device 4 (S31). For example, the CPU 21 of the determination apparatus 2 causes the communication unit 28 to transmit the authentication information to the storage device 4, and the CPU 41 of the storage device 4 determines whether or not the authentication information is valid, and performs processing for allowing the download of the learned data when the authentication information is valid and disallowing the download when the authentication information is not valid. In addition, for example, the CPU 21 of the determination apparatus 2 performs processing for paying a fee for using the learned data. The CPU 41 of the storage device 4 performs processing for allowing the download of the learned data when it is checked that the processing for payment has been performed and disallowing the download when it is not checked that the processing for payment has been performed. For example, the CPU 41 causes the communication unit 44 to transmit information indicating the authentication result to the determination apparatus 2 through the communication network 3.

When the authentication result that allows the download is obtained, the CPU 21 downloads the learned data from the storage device 4 through the communication network 3 by the communication unit 28 (S32). For example, the CPU 21 performs the processing of S32 when the information indicating the authentication result allowing the download is received through the communication unit 28. The process in S32 corresponds to a second acquisition unit. Then, the CPU 21 stores the downloaded learned data in the storage unit 24 (S33), and ends the process in which the determination apparatus 2 performs learning. In addition, the determination apparatus 2 may perform processing for uploading Raman spectrum data, training data, or learned data to the storage device 4.

Figure 12:
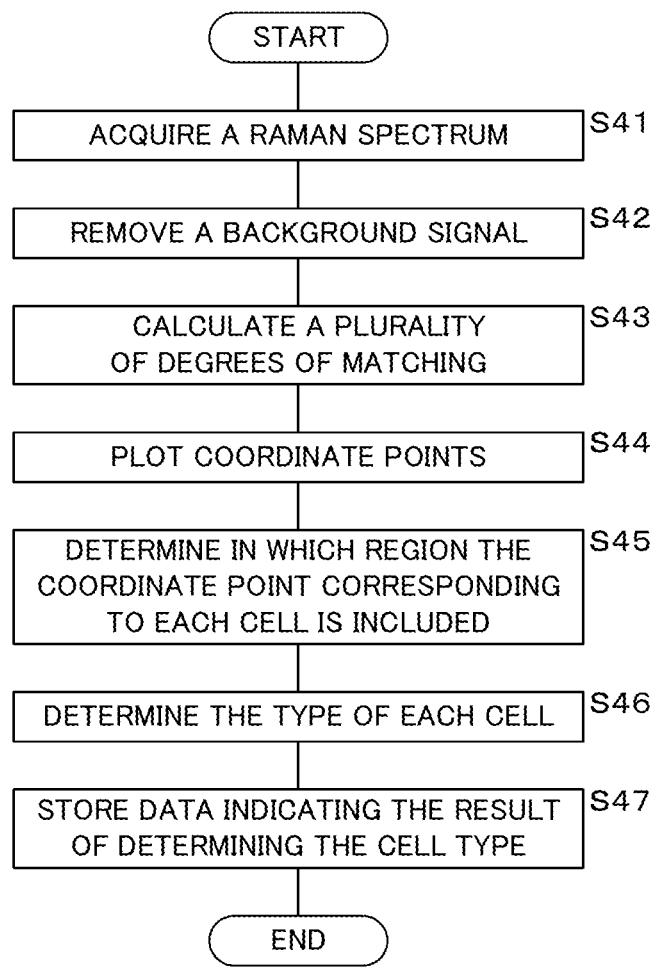
FIG. 12 is a flowchart illustrating the procedure of a process in which a determination apparatus determines a cell type.

In the present embodiment, the determination apparatus 2 determines the type of each cell contained in the sample 5 using the learned data. FIG. 12 is a flowchart illustrating the procedure of a process in which the determination apparatus 2 determines a cell type. The CPU 21 performs processing necessary for the determination apparatus 2 according to the computer program 241. The Raman scattered light measuring apparatus 1 acquires a Raman spectrum from the sample 5 containing one or more cells whose types have not been determined (S41). The Raman scattered light measuring apparatus 1 measures one Raman spectrum for each cell contained in the sample 5 as in the measurement in S11. One Raman spectrum is obtained when the number of cells to be determined is one, and a plurality of Raman spectra are obtained when the number of cells to be determined is plural. The control unit 18 outputs Raman spectrum data representing one or more Raman spectra, and the determination apparatus 2 receives the Raman spectrum data at the interface unit 27 and stores the Raman spectrum data in the storage unit 24.

Then, the CPU 21 performs background processing for removing a background signal from the acquired Raman spectra (S42). Then, the CPU 21 calculates a plurality of degrees of matching of the acquired Raman spectra with respect to the spectra of a plurality of principal components represented by the data included in the learned data (S43). The degree of matching is calculated by a method similar to that for the principal component score calculated in the principal component analysis. In S43, the CPU 21 calculates the degree of matching of the Raman spectrum of the cell whose type has not been determined with respect to the spectra of a plurality of principal components using the same calculation method as the calculation method for calculating a plurality of principal component scores for each of the plurality of Raman spectra in S12. The CPU 21 calculates, for one Raman spectrum, the same number of degrees of matching as the number of principal component scores calculated in S12. For example, the CPU 21 calculates a plurality of degrees of matching by performing a matrix calculation using a matrix used for calculating the principal component score in the matrix calculation in S12. For example, the CPU 21 calculates a first degree of matching, which is calculated by a calculation method similar to that for the first principal component score, and a second degree of matching, which is calculated by a calculation method similar to that for the second principal component score. The first degree of matching indicates how much the Raman spectrum of a cell whose type has not been determined matches the spectrum of the first principal component represented by the learned data, and the second degree of matching indicates how much the Raman spectrum matches the spectrum of the second principal component. The processing of S43 corresponds to a calculation unit.

Then, the CPU 21 plots, in the coordinate space, coordinate points having a plurality of degrees of matching corresponding to respective cells as coordinate components (S44). For example, the CPU 21 plots, on the two-dimensional coordinates, coordinate points having the first degree of matching and the second degree of matching as coordinate components. Then, the CPU 21 divides the coordinate space into a plurality of regions by the boundary 61 represented by the data included in the learned data, and determines in which region the coordinate point corresponding to each cell is included (S45).

Then, the CPU 21 determines the type of each cell corresponding to each region divided by the boundary 61 represented by the data included in the learned data as the type of each cell corresponding to the coordinate point determined to be included in each region, thereby determining the type of the cell (S46). The processing of S44 to S46 corresponds to a determination unit. Then, the CPU 21 stores data indicating the result of determining the cell type in the storage unit 24 (S47). The CPU 21 may display the result of determining the cell type on the display unit 26. As described above, the processing for determining the cell type is completed.

For example, the determination apparatus 2 is used to determine cells differentiated into a desired type by culturing and undifferentiated cells. Training data is created based on the Raman spectra obtained from cells determined to be differentiated and cells determined to be undifferentiated, and learning of the support vector machine is performed to create learned data. Thereafter, the Raman scattered light measuring apparatus 1 measures the Raman spectrum from the sample 5 containing the cultured cells, and the determination apparatus 2 determines whether each cell contained in the sample 5 is a cell differentiated into a desired type or an undifferentiated cell based on the learned data. When the type of each cell is determined by the support vector machine, the determination apparatus 2 can also determine the degree of cell differentiation depending on the distance between the boundary 61 and the coordinate point corresponding to each cell in the coordinate space.

For example, the determination apparatus 2 is used to determine whether or not the collected cells are normal types of cells. Training data is created based on the Raman spectra obtained from cells determined to be normal and cells determined to be abnormal, and learning of the support vector machine is performed to create learned data. Thereafter, the Raman scattered light measuring apparatus 1 measures the Raman spectrum from the sample 5 containing the collected cells, and the determination apparatus 2 determines whether or not each cell contained in the sample 5 is a normal cell based on the learned data. When the cell type is determined by the support vector machine, the determination apparatus 2 can also determine the degree of abnormality of the abnormal cell depending on the distance between the boundary 61 and the coordinate point corresponding to each cell in the coordinate space.

As described in detail above, in the present embodiment, one Raman spectrum is acquired from one cell, and the type of the cell is determined based on the acquired Raman spectrum. The time required for the determination is shortened as compared with a method of determining the cell type using the distribution of the Raman spectrum in the cell. By using the Raman spectra obtained one by one from each cell, processing for determination based on the characteristics of the entire cell can be performed without being affected by the detailed structure in the cell, compared with a case of using the distribution of Raman spectra in the cell.

In addition, in the present embodiment, the determination apparatus 2 performs principal component analysis of a plurality of Raman spectra obtained from a plurality of known types of cells, and classifies a plurality of principal component scores corresponding to each of the plurality of Raman spectra based on their types using the support vector machine. In addition, the determination apparatus 2 determines the cell type by classifying a plurality of degrees of matching corresponding to undetermined cells based on the classification result of the plurality of principal component scores corresponding to the plurality of known types of cells. From the same type of cells, Raman spectra having similar shapes tend to be obtained, and the principal component scores tend to be similar numerical values. Therefore, since a set of principal component scores corresponding to known types of cells can be classified, each cell is determined by classifying the degrees of matching corresponding to undetermined cells based on the classification result. Instead of focusing on some Raman bands included in the Raman spectrum as being characteristic of cells, the cell type is determined by comparing the overall characteristics of the Raman spectrum. Therefore, it is possible to determine the cell type more accurately and easily than before. In addition, the determination is performed using the support vector machine. Therefore, by performing the learning of the support vector machine, it is possible to improve the determination apparatus 2 so that the cell type can be determined more accurately.

Second Embodiment

In a second embodiment, a form in which cell determination is performed using a part of the Raman spectrum is shown. The Raman spectrum of a cell includes a portion, which reflects the characteristics of the cell relatively strongly and in which a change depending on the cell type is large, and includes a portion, which does not reflect the characteristics of the cell much and in which a change depending on the cell type is small. Hereinafter, a portion that strongly reflects the characteristics of the cell in the Raman spectrum of the cell is referred to as a fingerprint region. In the second embodiment, cell determination is performed using the fingerprint region.

FIG. 13 is a graph showing an example of a fingerprint region in the Raman spectra. The Raman spectra shown in FIG. 13 are the same as the Raman spectra shown in FIG. 4. The range of the fingerprint region is a range in which the Raman shift is 1250 to 1750 $cm^{-1}$. The fingerprint region reflects important information derived from components inside the cell, such as the secondary structure of cytochrome C, nucleic acid, lipid, or amide (such as amide I, II, or III). For this reason, the fingerprint region strongly reflects the characteristics of the cell, and changes greatly depending on the cell type as compared with other portions in the Raman spectrum.

Also in the second embodiment, the configuration of the Raman scattered light measuring apparatus 1 is the same as that in the first embodiment. As in the first embodiment, the Raman scattered light measuring apparatus 1 performs the learning of the support vector machine for determining the cell type by performing the processing of S11 to S17. In S11, the Raman scattered light measuring apparatus 1 acquires a plurality of Raman spectra by measuring a Raman spectrum one by one from each of the plurality of cells contained in the sample 5.

In S13, the CPU 21 of the determination apparatus 2 performs principal component analysis of a fingerprint region in a plurality of Raman spectra. That is, the CPU 21 performs principal component analysis of multidimensional data corresponding to the fingerprint region among a plurality of pieces of multidimensional data representing the plurality of Raman spectra. For example, in the matrix shown in FIG. 5, a matrix extracted from a portion corresponding to a range in which the Raman shift is 1250 to 1750 $cm^{-1}$ is a target of the principal component analysis. The CPU 21 performs calculation for generating the spectra of a plurality of principal components relevant to the fingerprint region, such as a spectrum of a first principal component relevant to the fingerprint region and a spectrum of a second principal component relevant to the fingerprint region, by the principal component analysis.

FIGS. 14A and 14B are graphs showing examples of the spectrum of the principal component relevant to the fingerprint region. FIGS. 14A and 14B show the results of principal component analysis for a plurality of Raman spectra obtained from a plurality of RBLs and a plurality of CHOs. FIG. 14A shows an example of the spectrum of the first principal component, and FIG. 14B shows an example of the spectrum of the second principal component. The horizontal axis indicates a Raman shift, and the vertical axis indicates the intensity of Raman scattered light at each Raman shift.

In S13, the CPU 21 further calculates, for each of the plurality of Raman spectra, a plurality of principal component scores relevant to the fingerprint region, such as a first principal component score relevant to the fingerprint region and a second principal component score relevant to the fingerprint region. The first principal component score relevant to the fingerprint region indicates the contribution ratio of the fingerprint region in one Raman spectrum to the spectrum of the first principal component relevant to the fingerprint region. A plurality of principal component scores relevant to the fingerprint region are obtained for each Raman spectrum and cell.

In addition, in S13, the determination apparatus 2 may generate a spectrum of the principal component for the range of the Raman shift wider than the range of the fingerprint region, extract a portion relevant to the fingerprint region from the spectrum of the principal component, and calculate a principal component score relevant to the fingerprint region using the extracted portion. In addition, the Raman scattered light measuring apparatus 1 may extract a fingerprint region from the Raman spectrum measured in S11 and perform the processing of S12 and subsequent steps on the data representing the extracted fingerprint region. In addition, when measuring the Raman spectrum in S11, the Raman scattered light measuring apparatus 1 may measure only the fingerprint region and perform the processing of S12 and subsequent steps on the data representing the measured fingerprint region. Whichever method is used, a plurality of principal component scores relevant to the fingerprint region can be obtained.

Then, in S14, the CPU 21 generates a coordinate space including coordinate points having a plurality of principal component scores relevant to the fingerprint region as coordinate components. For example, the CPU 21 plots, on the two-dimensional coordinates, a plurality of coordinate points having a first principal component score relevant to the fingerprint region and a second principal component score relevant to the fingerprint region as coordinate components. In S15, the CPU 21 performs the learning of the support vector machine using the cell information and a plurality of principal component scores relevant to the fingerprint region as training data. For example, in order to determine the cell type, the CPU 21 performs processing for dividing the coordinate space, which includes a plurality of coordinate points having a first principal component score relevant to the fingerprint region and a second principal component score relevant to the fingerprint region as coordinate components, into a plurality of regions using a support vector machine. As in the first embodiment, the CPU 21 adjusts the parameters of the support vector machine so as to divide the coordinate space so that coordinate points corresponding to different types of cells are included in different regions.

Figure 15:
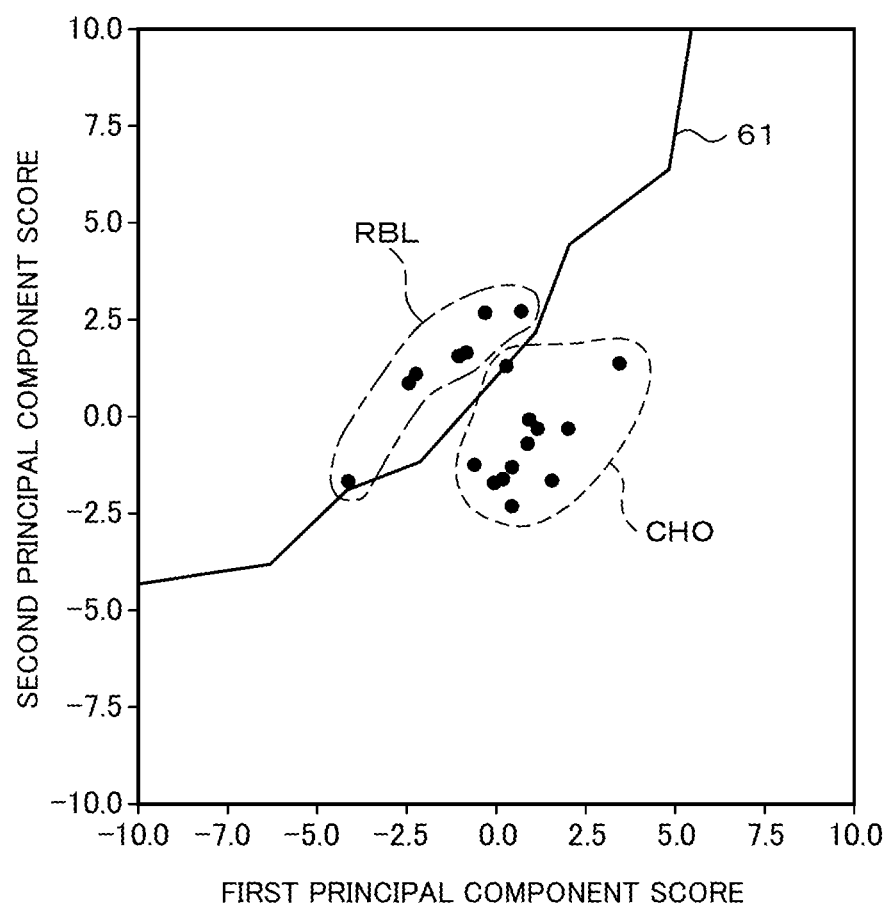
FIG. 15 is a characteristic diagram showing an example in which a coordinate space is divided by a support vector machine according to a second embodiment.

FIG. 15 is a characteristic diagram showing an example in which the coordinate space is divided by the support vector machine according to the second embodiment. The horizontal axis indicates the first principal component score relevant to the fingerprint region, and the vertical axis indicates the second principal component score relevant to the fingerprint region. In the diagram, a plurality of coordinate points having a first principal component score relevant to the fingerprint region and a second principal component score relevant to the fingerprint region as coordinate components are included in the two-dimensional coordinate space. FIG. 15 shows a plurality of coordinate points corresponding to a plurality of Raman spectra obtained from a plurality of RBLs and shows a plurality of coordinate points corresponding to a plurality of Raman spectra obtained from a plurality of CHOs. From the same type of cells, similar fingerprint regions are obtained, and the principal component scores relevant to the fingerprint regions are similar numerical values. For this reason, in the coordinate space, coordinate points corresponding to the same type of cells tend to be located close to each other, and coordinate points corresponding to different types of cells tend to be located away from each other. A plurality of coordinate points surrounded by the broken line correspond to a plurality of CHOs. A plurality of coordinate points surrounded by the one-dot chain line correspond to a plurality of RBLs. The CPU 21 adjusts the parameters of the support vector machine so that the two-dimensional coordinate space can be divided into a region including coordinate points corresponding to CHOs and a region including coordinate points corresponding to RBLs. FIG. 15 shows an example in which the boundary 61 of a plurality of divided regions are indicated by polygonal lines. In addition, the CPU 21 adjusts the parameters of the support vector machine so that the margin between the coordinate point and the boundary 61 in the coordinate space is as large as possible.

The CPU 21 performs the processing of S16 and S17 as in the first embodiment. As a result of S11 to S17, learned data including data indicating the spectrum of the principal component relevant to the fingerprint region, the boundary 61, and the type of each cell corresponding to each region divided by the boundary 61 is stored in the storage unit 24. As in the first embodiment, the determination apparatus 2 may perform processing for acquiring training data or learned data from the outside.

As in the first embodiment, the Raman scattered light measuring apparatus 1 performs the processing of S41 to S47 to determine the type of each cell contained in the sample 5 using the learned data. In S41, the Raman scattered light measuring apparatus 1 acquires one Raman spectrum for each cell contained in the sample 5. In S43, the CPU 21 of the determination apparatus 2 extracts a fingerprint region from the acquired Raman spectrum, and calculates the degree of matching of the extracted fingerprint region with respect to the spectrum of the principal component relevant to the fingerprint region represented by the data included in the learned data. The CPU 21 calculates the degree of matching relevant to the fingerprint region using the same calculation method as the calculation method for calculating the principal component score. The CPU 21 calculates, for one Raman spectrum, the same number of degrees of matching relevant to the fingerprint region as the number of principal component scores relevant to the fingerprint region. For example, the CPU 21 calculates a first degree of matching, which is calculated by a calculation method similar to that for the first principal component score, and a second degree of matching, which is calculated by a calculation method similar to that for the second principal component score.

In addition, when measuring the Raman spectrum in S41, the Raman scattered light measuring apparatus 1 may measure only the fingerprint region and perform the processing of S42 and subsequent steps on the data representing the measured fingerprint region. Also in this case, the degree of matching relevant to the fingerprint region can be obtained.

The CPU 21 performs the processing of S44 to S47 as in the first embodiment. By the processing of S41 to S47, the determination result of the type of each cell contained in the sample 5 is obtained. As described above, in the second embodiment, learning of the support vector machine and determination of a cell are performed using a fingerprint region in the Raman spectrum obtained from the cell. Since the fingerprint region strongly reflects the characteristics of the cell and greatly changes depending on the type of the cell, the determination apparatus 2 can cause the support vector machine to perform learning so that different types of cells can be more reliably classified by using the fingerprint region. By using this support vector machine, the determination apparatus 2 can more accurately determine the type of each cell.

In the first and second embodiments described above, a form in which the Raman scattered light measuring apparatus 1 irradiates the sample 5 with laser light is shown. However, the Raman scattered light measuring apparatus 1 may irradiate the sample 5 with excitation light other than the laser light in order to measure the Raman spectrum. In addition, in the first and second embodiments, a form is shown in which the sample 5 is moved to change a portion where Raman scattered light is generated in the sample 5. However, the Raman scattered light measuring apparatus 1 may change the optical path of excitation light in order to change a portion where Raman scattered light is generated in the sample 5.

In addition, in the first and second embodiments, a form is shown in which, in order to measure one Raman spectrum from one cell, one entire cell is irradiated with laser light and the Raman spectrum is measured. However, the Raman scattered light measuring apparatus 1 may sequentially irradiate a plurality of portions in one cell with excitation light, measure a plurality of Raman spectra for the plurality of portions in the one cell, and create one Raman spectrum representing the plurality of Raman spectra. For example, the Raman scattered light measuring apparatus 1 creates a Raman spectrum by averaging the plurality of Raman spectra. Also in this case, one Raman spectrum is measured from one cell. The Raman scattered light measuring apparatus 1 in which an optical system is set so as to sequentially irradiate a plurality of portions in one cell with excitation light can also be used to determine the cell type.

In addition, in the first and second embodiments, a form is shown in which the processing for dividing the two-dimensional coordinate space into a plurality of regions by the support vector machine is performed in order to determine the cell type. However, the determination apparatus 2 may perform processing for dividing a coordinate space of three or more dimensions into a plurality of regions. For example, in a form in which the determination apparatus 2 performs processing for dividing the three-dimensional coordinate space into a plurality of regions, a coordinate space including coordinate points having a first principal component score, a second principal component score, and a third principal component score as coordinate components and a coordinate space including coordinate points having first, second, and third degrees of matching as coordinate components are used, and the boundary 61 is a plane or a curved surface. In addition, in the first and second embodiments, a form is shown in which the support vector machine is used as a learning model using supervised learning. However, the determination apparatus 2 may use a learning model other than the support vector machine. For example, the determination apparatus 2 may use a convolutional neural network as a learning model using supervised learning. In addition, the determination apparatus 2 can be used not only for determining the cell type but also for determining a portion in a cell or a biological substance, such as determining the cell nucleus type or the protein type. In addition, in the first and second embodiments, a form is shown in which the Raman scattered light measuring apparatus 1 and the determination apparatus 2 are integrated to form an analyzer. However, the determination apparatus 2 may be separated from the Raman scattered light measuring apparatus 1.

The present invention is not limited to the content of the above-described embodiments, and various changes can be made within the scope of the claims. That is, embodiments obtained by combining technical means appropriately changed within the scope of the claims are also included in the technical scope of the present invention.

(Note 1)

A method of determining a type of each cell contained in a sample, comprising:

acquiring one Raman spectrum from one undetermined cell;

calculating a plurality of degrees of matching indicating a degree of matching of a portion, which corresponds to a predetermined Raman shift range of the Raman spectrum of the undetermined cell, with respect to a portion corresponding to the Raman shift range of spectra of a plurality of principal components obtained by principal component analysis of portions corresponding to the Raman shift range of a plurality of Raman spectra that are obtained one by one from each of a plurality of known types of cells; and determining a type of the undetermined cell by classifying the plurality of degrees of matching, based on a result obtained by classifying a plurality of principal component scores corresponding to each of the plurality of known types of cells obtained by the principal component analysis depending on the type of cells by a learning model using supervised learning.

(Note 2)

A method of performing learning for determining a type of each cell contained in a sample based on a Raman spectrum, comprising:

acquiring a portion corresponding to a predetermined Raman shift range of spectra of a plurality of principal components, which are obtained by principal component analysis of a portion corresponding to the Raman shift range of a plurality of Raman spectra that are obtained one by one from each of a plurality of known types of cells, and a plurality of principal component scores corresponding to each of the plurality of cells;

performing machine learning of a learning model so that a plurality of sets of the plurality of principal component scores can be classified depending on the type of cells by the learning model using supervised learning with, as training data, the plurality of sets of the plurality of principal component scores and each of the types of the plurality of cells; and storing the portion corresponding to the Raman shift range of spectra of the plurality of principal components and a result of classification of the plurality of principal component scores by the learning model after learning.

(Note 3)

An apparatus for determining a type of each cell contained in a sample, comprising:

a calculation unit that calculates a plurality of degrees of matching of a portion, which corresponds to a predetermined Raman shift range of a Raman spectrum acquired from an undetermined cell, with respect to a portion corresponding to the Raman shift range of spectra of a plurality of principal components obtained by principal component analysis of portions corresponding to the Raman shift range of a plurality of Raman spectra that are obtained one by one from each of a plurality of known types of cells; and a determination unit that determines a type of the undetermined cell by classifying the plurality of degrees of matching, based on a result obtained by classifying a plurality of principal component scores corresponding to each of the plurality of known types of cells obtained by the principal component analysis depending on the type of cells by a learning model using supervised learning.

(Note 4)

A computer program for causing a computer to execute a process for determining a type of each cell contained in a sample, the computer program causing the computer to execute a process including:

a step of calculating a plurality of degrees of matching indicating a degree of contribution of a portion, which corresponds to a predetermined Raman shift range of a Raman spectrum acquired from an undetermined cell, with respect to a portion corresponding to the Raman shift range of spectra of a plurality of principal components obtained by principal component analysis of portions corresponding to the Raman shift range of a plurality of Raman spectra that are obtained one by one from each of a plurality of known types of cells; and a step of determining a type of the undetermined cell by classifying the plurality of degrees of matching, based on a result obtained by classifying a plurality of principal component scores corresponding to each of the plurality of known types of cells obtained by the principal component analysis depending on the type of cells by a learning model using supervised learning.

(Note 5)

A computer program for causing a computer to perform learning for determining a type of each cell contained in a sample, the computer program causing the computer to execute a process including:

a step of acquiring a portion corresponding to a predetermined Raman shift range of spectra of a plurality of principal components, which are obtained by principal component analysis of a portion corresponding to the Raman shift range of a plurality of Raman spectra that are obtained one by one from each of a plurality of known types of cells, and a plurality of principal component scores corresponding to each of the plurality of cells;

a step of performing machine learning of a learning model so that the plurality of principal component scores can be classified depending on the type of cells by the learning model using supervised learning with, as training data, a plurality of sets of the plurality of principal component scores and each of the types of the plurality of cells; and a step of storing the portion corresponding to the Raman shift range of spectra of the plurality of principal components and a result of classification of the plurality of principal component scores by the learning model after learning.

(Note 6)

A learning method of learning for determining a type of each cell contained in a sample based on a Raman spectrum, comprising:

acquiring spectra of a plurality of principal components, which are obtained by principal component analysis of a plurality of Raman spectra that are obtained one by one from each of a plurality of known types of cells, and a plurality of principal component scores corresponding to each of the plurality of cells;

performing machine learning of a learning model so that a plurality of sets of the plurality of principal component scores are able to be classified depending on the type of the plurality of cells by the learning model using supervised learning with, as training data, the plurality of sets of the plurality of principal component scores and each of the types of the plurality of cells; and storing the spectra of the plurality of principal components and a result of classification of the plurality of principal component scores by the learning model after learning.

(Note 7)

The learning method according to Note 6, wherein the plurality of sets of the plurality of principal component scores are classified by dividing a coordinate space, in which a plurality of coordinate points having the plurality of principal component scores as coordinate components are included, into a plurality of regions by the learning model.

(Note 8)

A recording medium recording a computer program for causing a computer to perform learning for determining a type of each cell contained in a sample, the computer program causing the computer to execute a process including:

a step of acquiring spectra of a plurality of principal components, which are obtained by principal component analysis of a plurality of Raman spectra that are obtained one by one from each of a plurality of known types of cells, and a plurality of principal component scores corresponding to each of the plurality of cells;

a step of performing machine learning of a learning model so that the plurality of principal component scores are able to be classified depending on the type of the plurality of cells by the learning model using supervised learning with, as training data, a plurality of sets of the plurality of principal component scores and each of the types of the plurality of cells; and a step of storing the spectra of the plurality of principal components and a result of classification of the plurality of principal component scores by the learning model after learning.

It is to be noted that, as used herein and in the appended claims, the singular forms "a", "an", and "the" include plural referents unless the context clearly dictates otherwise.

It is to be noted that the disclosed embodiment is illustrative and not restrictive in all aspects. The scope of the present invention is defined by the appended claims rather than by the description preceding them, and all changes that fall within metes and bounds of the claims, or equivalence of such metes and bounds thereof are therefore intended to be embraced by the claims.

The invention claimed is:

1. A determination method of determining a type of each cell contained in a sample, comprising:
    acquiring one Raman spectrum from one undetermined cell;
    calculating a plurality of degrees of matching of a Raman spectrum of the undetermined cell with respect to spectra of a plurality of principal components obtained by principal component analysis of a plurality of Raman spectra that are obtained one by one from each of a plurality of known types of cells; and
    determining a type of the undetermined cell by classifying the plurality of degrees of matching, based on a result obtained by classifying a plurality of principal component scores corresponding to each of the plurality of known types of cells obtained by the principal component analysis depending on the type of cells by a learning model using supervised learning.

2. The determination method according to claim 1, wherein
    the learning model is a support vector machine.

3. The determination method according to claim 1, wherein
    the machine learning of the learning model is performed using, as training data, the plurality of principal component scores corresponding to each of the plurality of known types of cells and each of the types of the plurality of cells.

4. The determination method according to claim 1, wherein
    one entire cell is irradiated with excitation light, and
    a Raman spectrum is acquired by measuring Raman scattered light from the one entire cell.

5. A determination apparatus for determining a type of each cell contained in a sample, comprising:
    a processor; and a memory, wherein the processor is operable to:
    calculate a plurality of degrees of matching of a Raman spectrum acquired from an undetermined cell with respect to spectra of a plurality of principal components obtained by principal component analysis of a plurality of Raman spectra that are obtained one by one from each of a plurality of known types of cells; and
    determine a type of the undetermined cell by classifying the plurality of degrees of matching based on a result obtained by classifying a plurality of principal component scores corresponding to each of the plurality of known types of cells obtained by the principal component analysis depending on the type of cells by a learning model using supervised learning.

6. The determination apparatus according to claim 5, wherein the processor is further operable to
    perform machine learning of the learning model using, as training data, the plurality of principal component scores corresponding to each of the plurality of known types of cells and each of the types of the plurality of cells.

7. The determination apparatus according to claim 6, wherein the processor is further operable to
    acquire the training data from outside.

8. The determination apparatus according to claim 5, wherein the processor is further operable to
    acquire, from outside, the spectra of the plurality of principal components and a result, which is obtained by classifying the plurality of principal component scores corresponding to each of the plurality of known types of cells depending on the type of cells by the learning model.

9. A recording medium recording a computer program for causing a computer to execute a process for determining a type of each cell contained in a sample, the computer program causing the computer to execute a process including:
    a step of calculating a plurality of degrees of matching indicating a degree of contribution of a Raman spectrum acquired from an undetermined cell to spectra of a plurality of principal components obtained by principal component analysis of a plurality of Raman spectra that are obtained one by one from each of a plurality of known types of cells; and
    a step of determining a type of the undetermined cell by classifying the plurality of degrees of matching, based on a result obtained by classifying a plurality of principal component scores corresponding to each of the plurality of known types of cells obtained by the principal component analysis depending on the type of cells by a learning model using supervised learning.

* * * * *